US006916345B2

(12) United States Patent
Vidal et al.

(10) Patent No.: US 6,916,345 B2
(45) Date of Patent: Jul. 12, 2005

(54) 6-ALKOXY-2,3-DIAMINOPYRIDINE COUPLERS FOR DYEING KERATIN FIBRES

(75) Inventors: Laurent Vidal, Paris (FR); Aziz Fadli, Chelles (FR)

(73) Assignee: L'Oreal S.A., Paris (FR)

( * ) Notice: Subject to any disclaimer, the term of this patent is extended or adjusted under 35 U.S.C. 154(b) by 320 days.

(21) Appl. No.: 10/361,589

(22) Filed: Feb. 11, 2003

(65) Prior Publication Data
US 2003/0226216 A1 Dec. 11, 2003

Related U.S. Application Data
(60) Provisional application No. 60/372,453, filed on Apr. 16, 2002.

(30) Foreign Application Priority Data

Feb. 12, 2002 (FR) .......................................... 02 01710

(51) Int. Cl.$^7$ ................................................. A61K 7/13
(52) U.S. Cl. ..................... 8/405; 8/406; 8/408; 8/409; 8/410; 8/421; 8/568; 8/570; 8/571; 8/572; 8/573; 8/574; 8/575; 8/576; 548/400; 546/184; 546/249; 544/224; 540/484; 540/553
(58) Field of Search ................... 8/405, 406, 408, 8/409, 410, 421, 568, 570, 571, 572, 573, 574, 575, 576; 548/400; 546/184, 249; 544/224; 540/484, 553

(56) References Cited

U.S. PATENT DOCUMENTS 4,784,667 A    11/1988   Maak et al. ................... 8/409

FOREIGN PATENT DOCUMENTS

DE          19936442 A1  *  2/2001    ............ A61K/7/13
WO          WO 00/43392          7/2000

OTHER PUBLICATIONS

English abstract of the Patent No. DE 19936442 A1.*

STIC Search Report dated Feb. 10, 2005.*

Hervé Prunier et al., "Novel and Selective Partial Agonists of 5–HT$_3$ Receptors. 2. Synthesis and Biological Evaluation of Piperazinopyridopyrrolopyrazines, Piperazinopyrroloquinoxalines, and Piperazinopyridopyrroloquinoxalines," Journal of Medicinal Chemistry, vol. 40, No. 12, 1997, pp. 1808–1819.

* cited by examiner

*Primary Examiner*—Margaret Einsmann
*Assistant Examiner*—Eisa Elhilo
(74) *Attorney, Agent, or Firm*—Finnegan, Henderson, Farabow, Garrett & Dunner, L.L.P.

(57) ABSTRACT

Dye compositions for dyeing keratin fibers, comprising at least one oxidation base and at least one coupler chosen from 6-alkoxy-2,3-diaminopyridine derivatives of formula (I) as defined herein and the addition salts thereof; the use of the compositions for dyeing keratin fibers; and the dyeing processes using the compositions; as well as at least one entity chosen from novel 6-alkoxy-2,3-diaminopyridine compounds and their addition salts thereof that are useful as couplers.

26 Claims, No Drawings

6-ALKOXY-2,3-DIAMINOPYRIDINE COUPLERS FOR DYEING KERATIN FIBRES

This application claims benefit of U.S. Provisional Application No. 60/372,453, filed Apr. 16, 2002.

This disclosure relates to a dye composition for dyeing keratin fibers, comprising at least one oxidation base and at least one coupler of the 6-alkoxy-2,3-diaminopyridine type chosen from compounds of formula (I), as defined herein. This disclosure also relates to the use of the dye composition for dyeing keratin fibers and to the dyeing process using this composition. Further, this disclosure relates to at least one entity chosen from novel 6-alkoxy-2,3-diaminopyridine compounds and salts thereof and their use as couplers.

It is well-known practice to dye keratin fibers, such as human hair, with dye compositions comprising oxidation dye precursors, also known as oxidation bases, such as ortho- or para-phenylenediamines, ortho- or para-aminophenols and heterocyclic compounds. These oxidation bases may be colourless or weakly coloured compounds that, when combined with oxidizing products, can give rise to coloured compounds by a process of oxidative condensation.

It is also well-known that the shades obtained with these oxidation bases can be varied by combining them with couplers or coloration modifiers. The couplers or coloration modifiers may be chosen, for example, from aromatic meta-diamines, meta-aminophenols, meta-diphenols and certain heterocyclic compounds such as indole compounds.

The variety of molecules used as oxidation bases and couplers make it possible, for example, to obtain a wide range of colours.

The "permanent" coloration obtained by using these oxidation dyes should moreover satisfy a number of desirable characteristics. For example, the oxidation dyes should be free of toxicological drawbacks. Further, the dye compositions should allow, for example, shades to be obtained in the desired intensity. It further should show, for example, good resistance to external agents such as light, bad weather, washing, permanent-waving, perspiration and rubbing.

The dyes should be able to, for example, cover grey hair. Further, the oxidation dyes should be, for example, as unselective as possible, i.e. they should allow the smallest possible differences in coloration along the same length of keratin fibre, which is generally differently sensitized (i.e. damaged) between its end and its root.

Patent No. FR 1 397 551 discloses dye compositions comprising oxidation dye precursors of the tri-substituted pyridine derivative type, each of the substituents being optionally a hydroxyl, alkoxy or amino radical, or a radical $NR_1R_2$ with $R_1R_2$ being chosen from H, alkyl and aryl radicals. The coloration is obtained either by air-oxidation or using an oxidizing medium containing aqueous hydrogen peroxide solution at basic pH. On account of the high oxidizability of these pyridine precursors, the dyeing results obtained on hair may have tendency to change over time by changing colour, which may prove, for example, to be unattractive.

Patent Application No. DE 3 233 540 proposes to dye the hair with compositions comprising, as a coupler, 6-alkoxy-3-aminopyridine derivatives substituted in position 2 with a radical $NH_2$ or $NHR_3$, with $R_3$=H, $C_1$–$C_4$ alkyl, or $C_2$–$C_4$ hydroxyalkyl in combination with standard oxidation bases. These compositions may result, in the presence of certain bases, for example, para-phenylenediamine or para-tolylenediamine, in dark blue shades that may, for example, be sensitive to light and may, for example, lack the intensity and uniformity between the root and the end of the hair.

Patent Application No. DE 4 115 148 proposes dye compositions for the hair, comprising, as an oxidation base, a triaminopyrimidine derivative substituted with a fourth amino or hydroxyl radical, a meta-aminophenol and a 6-methoxy-3-aminopyridine derivative substituted in position 2 with a $C_1$–$C_4$ alkylamino radical. Such compositions give the hair a black coloration. However, shades such as coppery, mahogany, red, blue-violet or green, for example, may not be obtained with such compositions.

Patent Application No. FR 2 779 952 proposes to dye the hair with dye compositions based on pyridine derivatives as coupler and based on pyrazolo[1,5-a]-pyrimidines as oxidation bases. However, the coloration obtained with such compositions may not, for example, allow homogeneity (or uniformity) of the colour to be obtained from the root to the end of the hairs. Furthermore, it may, for example, lack intensity and chromaticity.

Patent Application No. EP 728 464 proposes to dye the hair with dye compositions based on 4,5- or 3,4-diaminopyrazoles as oxidation bases and pyridine derivatives as couplers. This solution makes it possible to obtain generally mahogany-coppery shades, but these shades may, for example, lack intensity and fastness with respect to external agents such as shampoo, light, sweat and chromaticity.

Patent Application No. DE 199 36 442 proposes a dye composition for dyeing human hair, comprising a para-aminophenol derivative as the oxidation base with at least one coupler derived from methylaminophenol and/or one coupler derived from 2-aminopyridine substituted in positions 3 and 6 with H, amino, hydroxyl or alkoxy radical. With such a composition, it may, for example, only be possible to dye hair that is naturally chestnut-coloured. Furthermore, the resulting dyeing may, for example, lack gloss and chromaticity.

The embodiments of this disclosure provide, for example, novel dye compositions for dyeing keratin fibers, that can overcome at least one of the drawbacks found in the prior art. For example, this disclosure provides compositions that may give at least one of the following results: powerful, uniform dyeing results between the root and the end of the hairs, with good chromaticity, and which can be relatively unselective and for example, resistant, while at the same time being capable of generating intense colorations in various shades, such as in the fundamental shades.

Disclosed herein is a dye composition comprising, in a medium suitable for dyeing, at least one oxidation base and at least one coupler chosen from 6-alkoxy-2,3-diaminopyridine derivatives of formula (I), and the addition salts thereof:

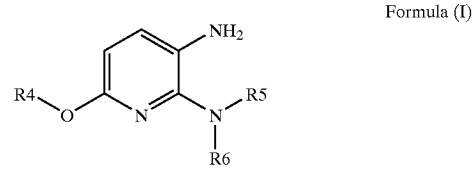

Formula (I)

wherein:

$R_4$ is chosen from $C_1$–$C_4$ alkyl radicals optionally substituted with at least one radical chosen from hydroxyl, $C_1$–$C_2$ alkoxy and $NR_7R_8$ radicals, wherein $R_7$ and $R_8$, which may be identical or different, are each chosen from hydrogen and $C_1$–$C_4$ alkyl, $C_2$–$C_6$ (poly) hydroxyalkyl, $C_2$–$C_6$ (poly)aminoalkyl and $C_2$–$C_6$ aminohydroxyalkyl radicals;

$R_5$ and $R_6$ form, together with the nitrogen atom to which they are attached, a carbon ring chosen from 5- to 8-membered rings, wherein at least one carbon atom of the 5- to 8-membered rings may be replaced with at least one entity chosen from an oxygen atom, an optionally substituted nitrogen atom, a sulphur atom, and a $SO_2$ group, and at least one carbon atom of the 5- to 8-membered rings may, independently of each other, be substituted; and said 5- to 8-membered rings do not comprise a peroxide bond, a diazo radical or a nitroso radical.

In one embodiment, $R_5$ and $R_6$ form, together with the nitrogen atom to which they are attached, a heterocycle chosen from 5- to 8-membered heterocycles chosen from pyrrolidine, piperidine, homopiperidine, piperazine, homopiperazine and diazepane.

In another embodiment, said 5- to 8-membered rings are optionally substituted with at least one radical chosen from the following radicals:

(i) $C_1$–$C_4$ alkyl optionally substituted with at least one radical chosen from hydroxyl, amino, $C_1$–$C_2$ (di)alkylamino and carboxyl radicals;
(ii) hydroxyl;
(iii) amino;
(iv) $C_1$–$C_2$ (di)alkylamino;
(v) carboxyl;
(vi) carboxamido; and
(vii) sulphonamido.

In another embodiment, $R_5$ and $R_6$ may form, together with the nitrogen to which they are attached, a heterocycle chosen from 2,5-dimethylpyrrolidine, proline, 3-hydroxyproline, 4-hydroxyproline, 2,4-dicarboxypyrrolidine, 3-hydroxy-2-hydroxymethylpyrrolidine, 2-carboxamidopyrrolidine, 3-hydroxy-2-carboxamidopyrrolidine, 2-(diethylcarboxamido)pyrrolidine, 2-hydroxymethylpyrrolidine, 3,4-dihydroxy-2-hydroxymethylpyrrolidine, 3-hydroxypyrrolidine, 3,4-dihydroxypyrrolidine, 3-amino-pyrrolidine, 3-methylaminopyrrolidine, 4-amino-3-hydroxypyrrolidine, 3-hydroxy-4-(2-hydroxyethyl)-aminopyrrolidine, 3-acetamidopyrrolidine, 3-(methylsulphonylamino)-pyrrolidine, piperidine, 2,6-dimethylpiperidine, 2-carboxypiperidine, 2-carboxamidopiperidine, 2-hydroxymethylpiperidine, 3-hydroxy-2-hydroxymethylpiperidine, 3-hydroxypiperidine, 4-hydroxypiperidine, 3-hydroxymethylpiperidine, homopiperidine, 2-carboxyhomopiperidine, 2-carboxamidohomopiperidine, diazepane, N-methyldiazepane and N-(2-hydroxyethyl)diazepane, and the addition salts thereof.

For example, $R_5$ and $R_6$ may form together with the nitrogen to which they are attached, a heterocycle chosen from pyrrolidine, 3-hydroxypyrrolidine, 3-aminopyrrolidine, 3-acetamidopyrrolidine, 3-(methylsulphonylamino)pyrrolidine, proline, 3-hydroxyproline, piperidine, hydroxypiperidine, homopiperidine, diazepane, N-methyldiazepane (also called N-methylhomopiperazine) and N-β-hydroxyethyldiazepane (also called N-β-hydroxyethylhomopiperazine), and the addition salts thereof.

As defined herein, the term "alkyl" means linear and branched radicals, such as methyl, ethyl, n-propyl, isopropyl, butyl, etc. An alkoxy radical is a radical alk-O wherein the alkyl radical has the same definition as given above. The term "halogen" means a halogen atom chosen, for example, from Cl, Br and I.

The (poly)aminoalkyl radicals are alkyl radicals substituted with at least one amino radical. The (poly) hydroxyalkyl radicals are alkyl radicals substituted with at least one hydroxyl substituent.

The at least one coupler chosen from 6-alkoxy-2,3-diaminopyridine derivatives of formula (I), for example, may be chosen from:

6-methoxy-2-pyrrolidin-1-ylpyrid-3-ylamine;
2-(2,5-dimethylpyrrolidin-1-yl)-6-methoxypyrid-3-ylamine;
6-methoxy-2-morpholin-4-ylpyrid-3-ylamine;
N-[1-(3-amino-6-methoxypyrid-2-yl)pyrrolidin-3-yl]acetamide;
6'-methoxy-3,4,5,6-tetrahydro-2H-[1,2']bipyridylyl-3'-ylamine;
2-(3'-amino-6'-methoxy-3,4,5,6-tetrahydro-2H-[1,2']bipyridylyl-2-yl)ethanol;
6-methoxy-2-(4-methylpiperazin-1-yl)pyrid-3-ylamine;
6'-methoxy-2-methyl-3,4,5,6-tetrahydro-2H-[1,2']bipyridylyl-3'-ylamine;
6'-methoxy-3-methyl-3,4,5,6-tetrahydro-2H-[1,2']bipyridylyl-3'-ylamine;
2-(3'-amino-6'-methoxy-3,4,5,6-tetrahydro-2H-[1,2']bipyridylyl-2-yl)ethanol; and the addition salts thereof.

In one embodiment, the at least one coupler chosen from 6-alkoxy-2,3-diaminopyridine derivatives of formula (I) may be chosen from 6-methoxy-2-pyrrolidin-1-ylpyrid-3-ylamine and the addition salts thereof.

The oxidation dye composition disclosed herein further comprises at least one oxidation base conventionally used in oxidation dyeing. For example, the at least one oxidation base may be chosen from para-phenylenediamines, bis(phenyl)alkylenediamines, para-aminophenols, ortho-aminophenols, heterocyclic bases, and the addition salts thereof.

The para-phenylenediamines may be chosen, for example, from para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, and the addition salts thereof.

The para-phenylenediamines may be chosen, for example, from para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-paraphenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, and the addition salts thereof.

The bis(phenyl)alkylenediamines may be chosen, for example, from N,N'-bis(β-hydroxyethyl)-N,N'-bis(4'-aminophenyl)-1,3-diaminopropanol, N,N'-bis(β-hydroxyethyl)-N,N'-bis(4'aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,6-dioxaoctane, and the addition salts thereof.

The para-aminophenols may be chosen, for example, from para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and the addition salts thereof.

The ortho-aminophenols may be chosen, for example, from 2-aminophenol, 2-amino-5-methylphenol, 2-amino-6-methylphenol, 5-acetamido-2-aminophenol, and the addition salts thereof.

The heterocyclic bases may be chosen, for example, from pyridine derivatives, pyrimidine derivatives, pyrazole derivatives and the addition salts thereof.

The pyridine derivatives may be chosen, for example, from those disclosed in Patent Nos. GB 1 026 978 and GB 1 153 196, such as 2,5-diaminopyridine, 2-(4-methoxyphenyl)amino-3-aminopyridie, 2,3-diamino-6-methoxypyridine, 2-(β-methoxyethyl)amino-3-amino-6-methoxypyridine, 3,4-diaminopyridine, and the addition salts thereof.

The pyrimidine derivatives may be chosen from those disclosed, for example, in Patent Nos. DE 2 359 399; JP 88-169 571; JP 05 163 124; and EP 0 770 375 and Patent Application No. WO 96/15765, such as 2,4,5,6-tetraaminopyrimidine, 4-hydroxy 2,5,6-triaminopyrimidine, 2-hydroxy-4,5,6-triaminopyrimidine, 2,4-dihydroxy-5,6-diaminopyrimidine, 2,5,6-triaminopyrimidine and pyrazolopyrimidine derivatives such as those described in Patent Application No. FR-A-2 750 048, for example, pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo-[1,5-a]pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)-(2-hydroxyethyl)amino]ethanol, 2-[(7-aminopyrazolo[1,5-a]pyrimidin-3-yl)-(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine, 3-amino-5-methyl-7-imidazolylpropylaminopyrazolo[1,5-a]pyrimidine, and the addition salts thereof and the tautomeric forms thereof, where a tautomeric equilibrium exists.

The pyrazole derivatives may be chosen, for example, from those disclosed in Patent Nos. DE 3 843 892 and DE 4 133 957 and Patent Application Nos. WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and the addition salts thereof.

The at least one oxidation base may be present in an amount ranging from 0.001% to 10% by weight, such as from 0.005% to 6% by weight, relative to the total weight of the dye composition.

The dye composition disclosed herein may further comprise at least one additional coupler chosen from those conventionally used for dyeing keratin fibers. The at least one additional coupler may be chosen, for example, from meta-phenylenediamines, meta-aminophenols, meta-diphenols, naphthalenic couplers, heterocyclic couplers, and the addition salts thereof.

The at least one additional coupler may be chosen, for example, from 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, and the addition salts thereof.

In one embodiment, the at least one additional coupler and the at least one coupler chosen from 6-alkoxy-2,3-diaminopyridine derivatives of formula (I) may each be present in an amount ranging, for example, from 0.001% to 10% by weight such as from 0.005% to 6% by weight, relative to the total weight of the dye composition.

The addition salts that may be used herein for the oxidation bases and couplers are chosen, for example, from the acid addition salts such as hydrochlorides, hydrobromides, sulphates, citrates, succinates, tartrates, lactates, tosylates, benzenesulphonates, phosphates and acetates, and base addition salts, such as sodium hydroxide, potassium hydroxide, aqueous ammonia, amines and alkanolamines.

The dye composition disclosed herein may also comprise at least one direct dye that may be chosen, for example, from nitrobenzene dyes, cationic direct dyes, azo direct dyes and methine direct dyes.

The medium suitable for dyeing, also known as the dye support, may be chosen from water and mixtures of water and at least one organic solvent to dissolve the compounds that would not be sufficiently soluble in water. The at least one organic solvent may be chosen, for example, from $C_1$–$C_4$ lower alkanols, such as ethanol and isopropanol; polyols and polyol ethers, such as 2-butoxyethanol, propylene glycol, propylene glycol monomethyl ether, diethylene glycol monomethyl ether and monoethyl ether, and aromatic alcohols, such as benzyl alcohol and phenoxyethanol.

The at least one organic solvent may be present in an amount ranging, for example, from 1% to 40% by weight, such as from 5% to 30% by weight, relative to the total weight of the dye composition.

The dye composition disclosed herein may further comprise at least one adjuvant chosen from adjuvants conventionally used in compositions for dyeing the hair, for example, anionic, cationic, nonionic, amphoteric and zwitterionic surfactants, anionic, cationic, nonionic, amphoteric and zwitterionic polymers, mineral and organic thickeners, such as anionic, cationic, nonionic and amphoteric polymeric associative thickeners, antioxidants, penetrating agents, sequestering agents, fragrances, buffers, dispersants, conditioning agents such as volatile and non-volatile, modified and unmodified silicones, film-forming agents, ceramides, preserving agents and opacifiers.

The at least one adjuvant may be present in an amount ranging, for example, from 0.01% and 20% by weight, relative to the total weight of the composition.

Needless to say, a person skilled in the art will take care to select at least one optional additional compound such that the advantageous properties intrinsically associated with the oxidation dye composition disclosed herein are not, or are not substantially, adversely affected by the envisaged addition.

The pH of the dye composition may, for example, range from 3 to 12, such as from 5 to 11. The pH may be adjusted, for example, to the desired value by using at least one entity chosen from acidifying agents and basifying agents chosen from those conventionally used in the dyeing of keratin fibers and standard buffer systems.

The acidifying agents may be chosen, for example, from mineral and organic acids, such as hydrochloric acid, orthophosphoric acid, sulphuric acid, carboxylic acids, such as acetic acid, tartaric acid, citric acid and lactic acid, and sulphonic acids.

The basifying agents may be chosen, for example, from aqueous ammonia, alkali metal carbonates, alkanolamines such as monoethanolamine, diethanolamine and triethanolamine and derivatives thereof, sodium hydroxide, potassium hydroxide and the compounds of formula (III) below:

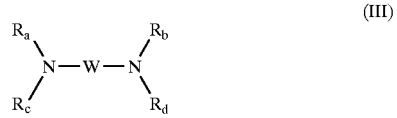

(III)

wherein W is chosen from propylene residues optionally substituted by at least one radical chosen from a hydroxyl radical and $C_1$–$C_4$ alkyl radicals; $R_a$, $R_b$, $R_c$ and $R_d$, which may be identical or different, are each chosen from hydrogen, $C_1$–$C_4$ alkyl and $C_1$–$C_4$ hydroxyalkyl radicals.

The dye composition disclosed herein may be in various forms, such as in a form chosen from liquids, creams and gels and in any other form that is suitable for dyeing keratin fibers, such as human hair.

Further disclosed herein is a dyeing process, comprising applying to keratin fibers the dye composition disclosed herein. And the colour may be developed with at least one oxidizing agent. The colour may be developed at acidic, neutral or alkaline pH. The at least one oxidizing agent may be mixed with the dye composition disclosed herein at the time of use or an oxidizing composition comprising the at least one oxidizing agent may, be applied simultaneously with or sequentially to the dye composition disclosed herein.

In one embodiment, the dye composition disclosed herein may be mixed, for example, at the time of use, with an oxidizing composition comprising, in a medium suitable for dyeing, at least one oxidizing agent, wherein the at least one oxidizing agent is present in an amount that is sufficient to develop a coloration. The mixture obtained may then be applied to the keratin fibers. After leaving it to act for a period ranging from 3 to 50 minutes, such as from 5 to 30 minutes, the keratin fibers may be rinsed, washed with shampoo, rinsed again and then dried.

The at least one oxidizing agent used for the oxidation dyeing of keratin fibers may be chosen, for example, from hydrogen peroxide, urea peroxide, alkali metal bromates, persalts such a perborates and persulphates, peracids and oxidase enzymes, such as peroxidases, 2-electron oxidoreductases such as uricases and 4-electron oxygenases, such as laccases. In one embodiment, the at least one oxidizing agent is hydrogen peroxide.

The oxidizing composition may further comprise, for example, at least one adjuvant chosen from those conventionally used in compositions for dyeing the hair, such as those adjuvants described above for the dye composition.

The pH of the oxidizing composition comprising the at least one oxidizing agent may be, for example, such that, after mixing with the dye composition, the pH of the resulting composition applied to the keratin fibers ranges from 3 to 12, such as from 5 to 11. The pH may be adjusted to the desired value using, for example, at least one entity chosen from acidifying and basifying agents conventionally used in the dyeing of keratin fibers, and standard buffer systems as defined above.

The ready-to-use composition that is finally applied to the keratin fibers may be in various forms, such as in a form chosen from liquids, creams and gels and any other form that is suitable for dyeing keratin fibers, such as human hair.

Further disclosed herein is a multi-compartment dyeing device or "kit", comprising a first compartment comprising the dye composition disclosed herein and a second compartment comprising the oxidizing composition. This device may be equipped, for example, with a means for applying the desired mixture to the hair, such as the devices disclosed in Patent No. FR-2 586 913.

Even further disclosed herein is at least one entity chosen from 6-alkoxy-2,3-diaminopyridine derivatives of formula (I) and the addition salts thereof as defined above with a proviso that the at least one entity is not chosen from 3-amino 6-methoxy 2-(4-methyl 2-propylimidazol-1-yl)-pyridine and 3-amino 6-methoxy 2-pyrrolo-pyridine.

The at least one coupler or entity chosen from 6-alkoxy-2,3-diaminopyridine derivatives of formula (I) and the addition salts thereof may be synthesized according to the following synthetic scheme:

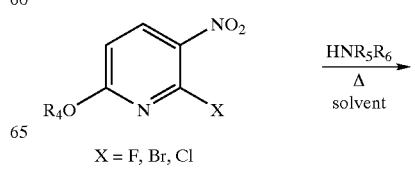

X = F, Br, Cl

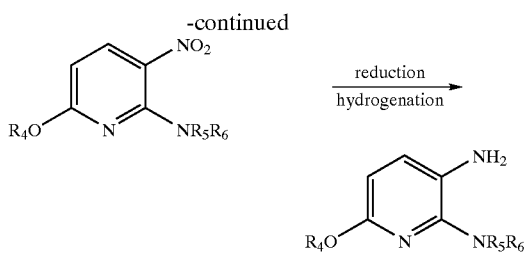

The first reaction comprises reacting a 6-alkoxy-3-nitro-2-halopyridine derivative with an amine of the type $HNR_5R_6$ wherein $R_5$ and $R_6$ have the meanings defined above, in a polar solvent with a boiling point ranging from 70° C. to 180° C. The reaction temperature varies depending on the pyridine derivatives and the nucleophilic amine, from 75° C. to 140° C. Alcohols chosen from ethanol, isopropanol, butanol, and pentanol, and acetic acid, formic acid, dioxane and DMF may, for example, be used as the solvent.

The second reaction comprises a reduction reaction performed either by hydrogenation under heterogeneous catalysis or by hydrogen transfer, or a reduction reaction performed with metal hydrides or with a formic acid/acetic acid pair in the presence of palladium.

For example, the method, widely illustrated in the literature, of hydrogenation catalyzed with palladium(0), Pd(II) or with Raney nickel of $PtO_2$ may, for example, be used.

Reduction by hydrogen transfer by reacting cyclohexene in the presence of palladium may also, for example, be used.

The examples that follow serve to illustrate embodiments of this disclosure without, however, being limiting in nature.

EXAMPLES OF SYNTHESIS

Example 1

6-methoxy-2-pyrrolidin-1-ylpyrid-3-ylamine

A) Synthesis of 6-methoxy-3-nitro-2-pyrrolidin-1-ylpyridine:

10 g (0.053 mol) of 2-chloro-3-nitro-6-methoxypyridine, 60 ml of ethanol and 7.54 g (0.1 mol) of pyrrolidine were placed in a fully equipped round-bottomed flask.

The mixture was refluxed for two hours with stirring and this reaction medium was then poured onto an ice/water mixture with stirring. The precipitate formed was suction-filtered and dried under vacuum to constant weight.

11.6 g of yellow powder was obtained (yield=98.3%, m.p.=82° C.).

Analysis by mass spectrometry and magnetic resonance spectroscopy: in accordance.

B) Synthesis of 6-methoxy-2-pyrrolidin-1-ylpyrid-3-ylamine

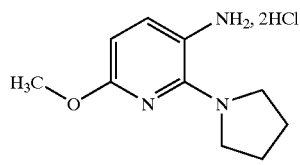

10 g (0.045 mol) of 6-methoxy-3-nitro-2-pyrrolidin-1-ylpyridine synthesized according to the above procedure, 150 ml of ethanol and 2 g of palladium-on-charcoal were placed in a hydrogenator.

The mixture was reduced for two hours under a pressure of 8 bar, the catalyst was then removed by filtration and the filtrate was acidified with hydrochloric acid.

After dilution with diisopropyl ether, the precipitate formed was suction-filtered and dried under vacuum to constant weight.

11 g of beige-coloured powder were obtained, yield= 92.3%.

Analysis by mass spectrometry and magnetic resonance spectroscopy: in accordance.

CHClNO analysis:

| | | | | | |
|---|---|---|---|---|---|
| Found | C 45.11 | H 6.68 | N 15.18 | O 9.86 | Cl 24.13 |
| Calculated | C 45.13 | H 6.44 | N 15.79 | O 6.01 | Cl 26.64 |

Example 2

2-(2,5-DIMETHYLPYRROLIDIN-1-YL)-6-METHOXYPYRID-3-YLAMINE

A) Synthesis of 2-(2,5-dimethylpyrrolidin-1-yl)-6-methoxy-3-nitropyridine:

4 g (0.0212 mol) of the product 2-chloro-3-nitro-6-methoxypyridine, 40 ml of ethanol and 4.2 g (0.042 mol) of 2,5-dimethylpyrrolidine were placed in a fully equipped round-bottomed flask.

The mixture was refluxed for two hours with stirring and was then poured onto an ice/water mixture with stirring. The precipitate formed was suction-filtered and dried under vacuum to constant weight.

4.93 g of yellow powder were obtained.

Analysis by mass spectrometry and magnetic resonance spectroscopy: in accordance.

B) Synthesis of 2-(2,5-dimethylpyrrolidin-1-yl)-6-methoxypyrid-3-ylamine

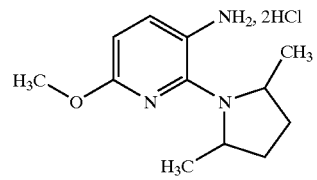

4.2 g (0.017 mol) of the product 2-(2,5-dimethylpyrrolidin-1-yl)-6-methoxy-3-nitropyridine synthesized according to the above procedure, 40 ml of ethanol, 10 ml of cyclohexene and 1.5 g of palladium-on-charcoal were placed in a fully equipped round-bottomed flask.

The mixture was refluxed for two hours with stirring, the catalyst was then removed by filtration and the filtrate was then acidified with hydrochloric acid. After dilution with diisopropyl ether, the precipitate formed was suction-filtered and dried under vacuum to constant weight.

4.28 g of powder were obtained; yield=89.2%.

Analysis by mass spectrometry and magnetic resonance spectroscopy: in accordance.

CHClNO analysis:

| | | | | | |
|---|---|---|---|---|---|
| Found | C 54.05 | H 7.26 | N 15.57 | O 11.66 | Cl 11.68 |
| Calculated | C 55.92 | H 7.82 | N 16.3 | O 6.21 | Cl 13.75 |

Example 3

6-methoxy-2-morpholin-4-ylpyrid-3-ylamine

A) Synthesis of: 4-(6-methoxy-3-nitropyrid-2-yl) morpholine 5 g (0.0265 mol) of the product 2-chloro-3-nitro-6-methoxypyridine, 50 ml of ethanol and 4.62 ml (0.053 mol) of morpholine were placed in a fully equipped round-bottomed flask.

The mixture was refluxed for two hours with stirring and was then poured onto an ice/water mixture with stirring. The precipitate formed was suction-filtered and dried under vacuum to constant weight.

6.32 g of yellow powder were obtained.

Analysis by mass spectrometry and magnetic resonance spectroscopy: in accordance.

B) Synthesis of 6-methoxy-2-morpholin-4-ylpyrid-3-ylamine

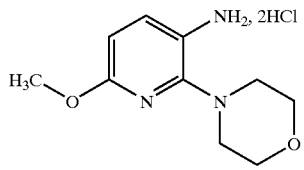

6.19 g (0.026 mol) of the product 4-(6-methoxy-3-nitropyrid-2-yl)morpholine synthesized according to the above procedure, 50 ml of ethanol, 20 ml of cyclohexene and 2 g of palladium-on-charcoal were placed in a fully equipped round-bottomed flask.

The mixture was refluxed for two hours with stirring, the catalyst was then removed by filtration and the filtrate was then acidified with hydrochloric acid. After dilution with diisopropyl ether, the precipitate formed was suction-filtered and dried under vacuum to constant weight.

6.21 g of yellow powder was obtained; yield=98.1%.

Analysis by mass spectrometry and magnetic resonance spectroscopy: in accordance.

CHClNO analysis:

| Found | C 42.49 | H 6.40 | N 14.17 | O 15.70 | Cl 21.82 |
|---|---|---|---|---|---|
| Calculated | C 42.57 | H 6.07 | N 14.89 | O 11.34 | Cl 25.13 |

Example 4

N-[1-(3-amino-6-methoxypyrid-2-yl)pyrrolidin-3-yl]acetamide

A) Synthesis of: N-[1-(6-methoxy-3-nitropyrid-2-yl)pyrrolidin-3-yl]acetamide 2 g (0.01 mol) of the product 2-chloro-3-nitro-6-methoxypyridine, 30 ml of dioxane, 5 ml of water and 2.56 g (0.2 mol) of 3-acetamidopyrrolidine were placed in a fully equipped round-bottomed flask.

The mixture was refluxed for two hours with stirring and was then poured onto an ice/water mixture with stirring. The precipitate formed was suction-filtered and dried under vacuum to constant weight.

2.51 g of yellow powder were obtained.

Analysis by mass spectrometry and magnetic resonance spectroscopy: in accordance.

B) Synthesis of N-[1-(3-amino-6-methoxypyrid-2-yl)pyrrolidin-3-yl]acetamide

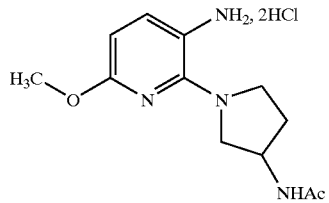

2.35 g (0.0084 mol) of the product N-[1-(6-methoxy-3-nitropyrid-2-yl)pyrrolidin-3-yl]acetamide synthesized according to the above procedure, 15 ml of ethanol, 7 ml of cyclohexene and 0.7 g of palladium-on-charcoal were placed in a fully equipped round-bottomed flask.

The mixture was refluxed for two hours with stirring, the catalyst was then removed by filtration and the filtrate was then acidified with hydrochloric acid. After dilution with diisopropyl ether, the precipitate formed was suction-filtered and dried under vacuum to constant weight.

2.05 g of brown powder was obtained.

Analysis by mass spectrometry and magnetic resonance spectroscopy: in accordance.

CHClNO analysis:

| Found | C 50.26 | H 6.68 | N 19.54 | O 11.16 | Cl 12.36 |
|---|---|---|---|---|---|
| Calculated | C 50.16 | H 6.83 | N 19.42 | O 11.30 | Cl 12.42 |

Example 5

6'-methoxy-3,4,5,6-tetrahydro-2H-[1,2']bipyridylyl-3'-ylamine

A) Synthesis of: 6'-methoxy-3'-nitro-3,4,5,6-tetrahydro-2H-[1,2']bypyridylyl:

1.9 g (0.01 mol) of the product 2-chloro-3-nitro-6-methoxypyridine, 30 ml of dioxane, 5 ml of water and 1.98 ml (0.02 mol) of piperidine were placed in a fully equipped round-bottomed flask.

The mixture was refluxed for two hours with stirring and was then poured onto an ice/water mixture with stirring. The precipitate formed was suction-filtered and dried under vacuum to constant weight.

2.14 g of yellow powder was obtained.

Analysis by mass spectrometry and magnetic resonance spectroscopy: in accordance.

B) Synthesis of 6'-methoxy-3,4,5,6-tetrahydro-2H-[1,2']bipyridylyl-3'-ylamine:

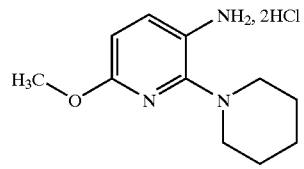

2 g (0.0084 mol) of the product 6'-methoxy-3'-nitro-3,4,5,6-tetrahydro-2H-[1,2']bypyridylyl synthesized according to the above procedure, 50 ml of ethanol, 5 ml of cyclohexene and 0.5 g of palladium-on-charcoal were placed in a fully equipped round-bottomed flask.

The mixture was refluxed for two hours with stirring, the catalyst was then removed by filtration and the filtrate was then acidified with hydrochloric acid. After dilution with diisopropyl ether, the precipitate formed was suction-filtered and dried under vacuum to constant weight.

1.57 g of powder was obtained; yield=77%.

Analysis by mass spectrometry and magnetic resonance spectroscopy: in accordance.

CHClNO analysis:

| Found | C 47.19 | H 6.81 | N 14.81 | O 6.45 | Cl 25.44 |
|---|---|---|---|---|---|
| Calculated | C 47.15 | H 6.83 | N 15 | O 5.71 | Cl 25.31 |

Example 6

2-(3'-amino-6'-methoxy-3,4,5,6-tetrahydro-2H-[1,2']bipyridylyl-2-yl)ethanol

A) Synthesis of: 2-(6'-methoxy-3'-nitro-3,4,5 6-tetrahydro-2H-[1,2']bipyridylyl-2-yl)ethanol:

5 g (0.0265 mol) of the product 2-chloro-3-nitro-6-methoxypyridine, 50 ml of ethanol and 6.78 ml (0.053 mol) of pyrrolidine were placed in a fully equipped round-bottomed flask.

The mixture was refluxed for two hours with stirring and was then poured onto an ice/water mixture with stirring. The precipitate formed was suction-filtered and dried under vacuum to constant weight.

7.01 g of yellow powder was obtained; yield=94.1%.

Analysis by mass spectrometry and magnetic resonance spectroscopy: in accordance.

B) Synthesis of 2-(3'-amino-6'-methoxy-3,4,5,6-tetrahydro-2H-[1,2']bipyridylyl-2-yl)ethanol:

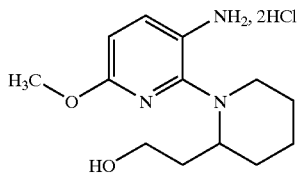

6.5 g (0.023 mol) of the product 2-(6'-methoxy-3'-nitro-3,4,5,6-tetrahydro-2H-[1,2']bipyridylyl-2-yl)ethanol synthesized according to the above procedure, 50 ml of ethanol, 20 ml of cyclohexene and 1.5 g of palladium-on-charcoal were placed in a fully equipped round-bottomed flask.

The mixture was refluxed for two hours with stirring, the catalyst was then removed by filtration and the filtrate was then acidified with hydrochloric acid. After dilution with diisopropyl ether, the precipitate formed was suction-filtered and dried under vacuum to constant weight.

6.46 g of powder was obtained; yield=97.9%.

Analysis by mass spectrometry and magnetic resonance spectroscopy: in accordance.

CHClNO analysis:

| | | | | | |
|---|---|---|---|---|---|
| Found | C 48.02 | H 7.23 | N 12.25 | O 12.41 | Cl 19.36 |
| Calculated | C 48.15 | H 7.15 | N 12.96 | O 9.87 | Cl 21.87 |

Example 7

6-methoxy-2-(4-methylpiperazin-1-yl)pyrid-3-ylamine

A) Synthesis of 1-(6-methoxy-3-nitropyrid-2-yl)-4-methylpiperazine:

1.9 g (0.01 mol) of the product 2-chloro-3-nitro-6-methoxypyridine, 30 ml of dioxane, 5 ml of water and 2.21 ml (0.02 mol) of 1-methylpiperidine were placed in a fully equipped round-bottomed flask.

The mixture was refluxed for two hours with stirring and was then poured onto an ice/water mixture with stirring. The precipitate formed was suction-filtered and dried under vacuum to constant weight.

1.022 g of yellow powder was obtained; yield=41%.

Analysis by mass spectrometry and magnetic resonance spectroscopy: in accordance.

B) Synthesis of 6-methoxy-2-(4-methylpiperazin-1-yl)pyrid-3-ylamine

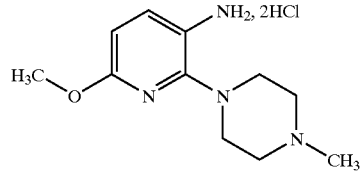

1.30 g (0.0052 mol) of the product 1-(6-methoxy-3-nitropyrid-2-yl)-4-methylpiperazine synthesized according to the above procedure, 25 ml of ethanol, 5 ml of cyclohexene and 0.6 g of palladium-on-charcoal were placed in a fully equipped round-bottomed flask.

The mixture was refluxed for two hours with stirring, the catalyst was then removed by filtration and the filtrate was then acidified with hydrochloric acid. After dilution with diisopropyl ether, the precipitate formed was suction-filtered and dried under vacuum to constant weight.

1.024 g of powder was obtained; yield=77%.

Analysis by mass spectrometry and magnetic resonance spectroscopy: in accordance.

CHNOCl analysis:

| | | | | | |
|---|---|---|---|---|---|
| Found | C 43.12 | H 7.02 | N | O 9.47 | Cl 22.77 |
| Calculated | C 44.76 | H 6.83 | N 18.98 | O 5.42 | Cl 24.02 |

Example 8

6'-methoxy-2-methyl-3,4,5,6-tetrahydro-2H-[1,2']bypyridylyl)-3'-ylamine

A) Synthesis of: 6'-methoxy-2-methyl-3'-nitro-3,4,5,6-tetrahydro-2H-[1,2']bypyridylyl:

5 g (0.027 mol) of the product 2-chloro-3-nitro-6-methoxypyridine, 50 ml of ethanol and 6.26 ml (0.053 mol) of 2-methylpiperidine were placed in a fully equipped round-bottomed flask.

The mixture was refluxed for two hours with stirring and was then poured onto an ice/water mixture with stirring. The precipitate formed was suction-filtered and dried under vacuum to constant weight.

6.48 g of yellow powder was obtained; yield=100%.

Analysis by mass spectrometry and magnetic resonance spectroscopy: in accordance.

B) Synthesis of 6'-methoxy-2-methyl-3,4,5,6-tetrahydro-2H-[1,2']bypyridylyl-3'-ylamine

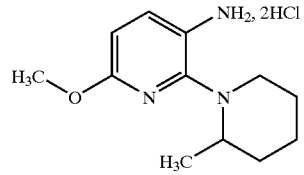

5 g (0.02 mol) of the product 6'-methoxy-2-methyl-3'-nitro-3,4,5,6-tetrahydro-2H -[1,2']bypyridylyl synthesized according to the above procedure, 50 ml of ethanol, 20 ml of cyclohexene and 1.5 g of palladium-on-charcoal were placed in a fully equipped round-bottomed flask.

The mixture was refluxed for two hours with stirring, the catalyst was then removed by filtration and the filtrate was then acidified with hydrochloric acid. After dilution with diisopropyl ether, the precipitate formed was suction-filtered and dried under vacuum to constant weight.

5.1 g of powder was obtained; yield=100%.

Analysis by mass spectrometry and magnetic resonance spectroscopy: in accordance.

CHClNO analysis:

| | | | | | |
|---|---|---|---|---|---|
| Found | C 48.79 | H 7.16 | N 14.04 | O 7.04 | Cl 22.01 |
| Calculated | C 48.99 | H 7.19 | N 14.28 | O 5.44 | Cl 24.1 |

Example 9

6'-methoxy-3-methyl-3,4,5,6-tetrahydro-2H-[1,2'] bipyridylyl-3'-ylamine

A) Synthesis of 6'-methoxy-3-methyl-3'-nitro-3,4,5,6-tetrahydro-2H-[1,2']bypyridylyl 5 g (0.027 mol) of the product 2-chloro-3-nitro-6-methoxypyridine, 50 ml of ethanol and 6.26 ml (0.053 mol) of 2-methylpiperidine were placed in a fully equipped round-bottomed flask.

The mixture was refluxed for two hours with stirring and was then poured onto an ice/water mixture with stirring. The precipitate formed was suction-filtered and dried under vacuum to constant weight.

6.41 g of yellow powder was obtained; yield=96.4%.

Analysis by mass spectrometry and magnetic resonance spectroscopy: in accordance.

B) Synthesis of 6'-methoxy-3-methyl-3,4,5,6-tetrahydro-2H-[1,2']bipyridylyl-3'-ylamine

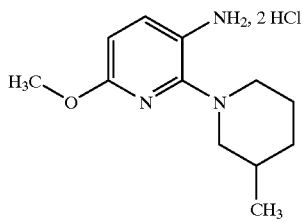

6.25 g (0.025 mol) of the product 6'-methoxy-3-methyl-3'-nitro-3,4,5,6-tetrahydro-2H-[1,2']bypyridylyl synthesized according to the above procedure, 50 ml of ethanol, 20 ml of cyclohexene and 2.0 g of palladium-on-charcoal were placed in a fully equipped round-bottomed flask.

The mixture was refluxed for two hours with stirring, the catalyst was then removed by filtration and the filtrate was then acidified with hydrochloric acid. After dilution with diisopropyl ether, the precipitate formed was suction-filtered and dried under vacuum to constant weight.

5.51 g of powder was obtained; yield=86%.

Analysis by mass spectrometry and magnetic resonance spectroscopy: in accordance.

CHClNO analysis:

| Found | C 50.31 | H 7.22 | N 13.99 | O 7.33 | Cl 20.16 |
|---|---|---|---|---|---|
| Calculated | C 48.99 | H 7.19 | N 14.28 | O 5.44 | Cl 24.1 |

Example 10

2-(3'-amino-6'-methoxy-3,4,5,6-tetrahydro-2H-[1,2'] bipyridylyl-2-yl)ethanol

A) Synthesis of 2-(6'-methoxy-3'-nitro-3,4,5,6-tetrahydro-2H-[1,2']bipyridylyl-2-yl)ethanol:

5 g (0.027 mol) of the product 2-chloro-3-nitro-6-methoxypyridine, 50 ml of ethanol and 6.78 ml (0.053 mol) of 2-piperidineethanol were placed in a fully equipped round-bottomed flask.

The mixture was refluxed for two hours with stirring and was then poured onto an ice/water mixture with stirring. The precipitate formed was suction-filtered and dried under vacuum to constant weight.

7.01 g of yellow powder was obtained; yield=94.1%.

Analysis by mass spectrometry and magnetic resonance spectroscopy: in accordance.

B) Synthesis of 2-(3'-amino-6'-methoxy-3,4,5,6-tetrahydro-2H-[1,2']bipyridylyl-2-yl)ethanol

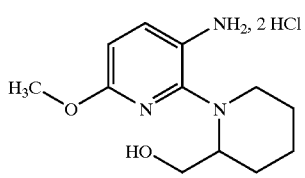

6.5 g (0.023 mol) of the product 2-(6'-methoxy-3'-nitro-3,4,5,6-tetrahydro-2H-[1,2']bipyridylyl-2-yl)ethanol synthesized according to the above procedure, 50 ml of ethanol, 20 ml of cyclohexene and 1.5 g of palladium-on-charcoal were placed in a fully equipped round-bottomed flask.

The mixture was refluxed for two hours with stirring, the catalyst was then removed by filtration and the filtrate was then acidified with hydrochloric acid. After dilution with diisopropyl ether, the precipitate formed was suction-filtered and dried under vacuum to constant weight.

6.46 g of powder was obtained; yield=97.9%.

Analysis by mass spectrometry and magnetic resonance spectroscopy: in accordance.

CHClNO analysis:

| Found | C 48.02 | H 7.23 | N 12.25 | O 12.41 | Cl 19.36 |
|---|---|---|---|---|---|
| Calculated | C 48.16 | H 7.15 | N 12.96 | O 9.87 | Cl 21.87 |

DYEING EXAMPLES

The dye compositions below were prepared:

| | Examples | |
|---|---|---|
| | 1 | 2 |
| Para-Phenylenediamine | $5 \times 10^{-3}$ mol | — |
| N,N-bis(2-hydroxyethyl)-p-phenylenediamine | — | $5 \times 10^{-3}$ mol |
| 6-Methoxy-2-pyrrolidin-1-ylpyrid-3-ylamine | $5 \times 10^{-3}$ mol | $5 \times 10^{-3}$ mol |
| Dye support | (1) | (1) |
| Demineralized water    qs | 100 g | 100 g |

Dye Support (1) pH 7

| 96° Ethyl alcohol | 20 g |
|---|---|
| Sodium metabisulphite as an aqueous 35% solution | 0.2275 g A.M. |
| Pentasodium salt of diethylenetriaminopentaacetic acid | 0.48 g A.M. |
| $C_8$–$C_{15}$ alkyl polyglucoside sold as a 60% solution under the name Oramix CG 110 by the company SEPPIC | 3.6 g A.M. |
| Benzyl alcohol | 2.0 g |
| Polyethylene glycol comprising 8 mol of EO | 3.0 g |
| $K_2HPO_4$ | 20.9 g |
| $KH_2PO_4$ | 10.88 g |

At the time of use, each composition was mixed with an equal weight of 20-volumes aqueous hydrogen peroxide solution (6% by weight). A final pH of 7, or 9.5, was obtained depending on the support used.

Each mixture obtained was applied to locks of grey hair comprising 90% white hairs. After an action time of 30 minutes, the locks were washed with a standard shampoo, rinsed and then dried.

Each lock was evaluated before and after dyeing, in the L*a*b* system, using a Minolta CM 2002® spectrophotometer (Luminant D65).

In the L*a*b* space, the clarity is indicated by the value L* on a scale from 0 to 100, while the chromatic coordinates are expressed by a* and b* which indicate two colour axes, a* the red-green axis, and b* the yellow-blue axis.

According to this system, the larger the value of L, the paler and less intense the colour. Conversely, the smaller the value of L, the darker or more intense the colour.

The dyeing results below were obtained:

|  | Natural hair | | |
| --- | --- | --- | --- |
|  | L* | a* | b* |
| Example 1 | 22.24 | 0.1 | −3.4 |
| Example 2 | 29.75 | −6.68 | −9.3 |

What is claimed is:

1. A dye composition comprising, in a medium suitable for dyeing:
   at least one oxidation base, and
   at least one coupler chosen from 6-alkoxy-2,3-diaminopyridine derivatives of formula (I) and the addition salts thereof:

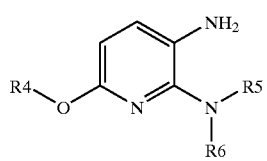

Formula (I)

wherein:
   $R_4$ is chosen from $C_1$–$C_4$ alkyl radicals optionally substituted with at least one radical chosen from hydroxyl, $C_1$–$C_2$ alkoxy and $NR_7R_8$ radicals, wherein $R_7$ and $R_8$, which may be identical or different, are each chosen from hydrogen and $C_1$–$C_4$ alkyl, $C_2$–$C_6$ (poly)hydroxyalkyl, $C_2$–$C_6$ (poly)aminoalkyl and $C_2$–$C_6$ aminohydroxyalkyl radicals;
   $R_5$ and $R_6$ form, together with the nitrogen atom to which they are attached, a carbon ring chosen from 5- to 8-membered rings, wherein at least one carbon atom of the 5- to 8-membered rings may be replaced with at least one entity chosen from an oxygen atom, an optionally substituted nitrogen atom, a sulphur atom, and an $SO_2$ group; at least one carbon atom of the 5- to 8-membered rings may, independently of each other, be substituted; and said 5- to 8-membered rings do not comprise a peroxide bond, a diazo radical or a nitroso radical.

2. The composition according to claim 1, wherein $R_5$ and $R_6$ form, together with the nitrogen atom to which they are attached, a heterocycle chosen from 5- to 8-membered heterocycles chosen from pyrrolidine, piperidine, homopiperidine, piperazine, homopiperazine and diazepane heterocycles.

3. The composition according to claim 1, wherein the 5- to 8-membered rings are optionally substituted with at least one radical chosen from the following radicals:
   (i) $C_1$–$C_4$ alkyl optionally substituted with at least one radical chosen from hydroxyl, amino, $C_1$–$C_2$ (di)alkylamino and carboxyl radicals;
   (ii) hydroxyl;
   (iii) amino;
   (iv) $C_1$–$C_2$ (di)alkylamino;
   (v) carboxyl;
   (vi) carboxamido; and
   (vii) sulphonamido.

4. The composition according to claim 1, wherein $R_5$ and $R_6$ form, together with the nitrogen to which they are attached, a heterocycle chosen from 2,5-dimethylpyrrolidine, proline, 3-hydroxyproline, 4-hydroxyproline, 2,4-dicarboxypyrrolidine, 3-hydroxy-2-hydroxymethylpyrrolidine, 2-carboxamidopyrrolidine, 3-hydroxy-2-carboxamidopyrrolidine, 2-(diethylcarboxamido)pyrrolidine, 2-hydroxymethylpyrrolidine, 3,4-dihydroxy-2-hydroxymethylpyrrolidine, 3-hydroxypyrrolidine, 3,4-dihydroxypyrrolidine, 3-amino-pyrrolidine, 3-methylaminopyrrolidine, 4-amino-3-hydroxypyrrolidine, 3-hydroxy-4-(2-hydroxyethyl)-aminopyrrolidine, 3-acetamidopyrrolidine, 3-(methylsulphonylamino)-pyrrolidine, piperidine, 2,6-dimethylpiperidine, 2-carboxypiperidine, 2-carboxamidopiperidine, 2-hydroxymethylpiperidine, 3-hydroxy-2-hydroxymethylpiperidine, 3-hydroxypiperidine, 4-hydroxypiperidine, 3-hydroxymethylpiperidine, homopiperidine, 2-carboxyhomopiperidine, 2-carboxamidohomopiperidine, diazepane, N-methyldiazepane, N-(2-hydroxyethyl)diazepane, and the addition salts thereof.

5. The composition according to claim 1, wherein $R_5$ and $R_6$ form, together with the nitrogen to which they are attached, a heterocycle chosen from pyrrolidine, 3-hydroxypyrrolidine, 3-aminopyrrolidine, 3-acetamidopyrrolidine, 3-(methylsulphonylamino)-pyrrolidine, proline, 3-hydroxyproline, piperidine, hydroxypiperidines, homopiperidine, diazepane, N-methyldiazepane, N-β-hydroxyethyldiazepane, and the addition salts thereof.

6. The composition according to claim 1, wherein the at least one coupler is chosen from:
   6-methoxy-2-pyrrolidin-1-ylpyrid-3-ylamine;
   2-(2,5-dimethylpyrrolidin-1-yl)-6-methoxypyrid-3-ylamine;
   6-methoxy-2-morphoin-4-ylpyrid-3-ylamine;
   N-[1-(3-amino-6-methoxypyrid-2-yl)pyrrolidin-3-yl]acetamide;
   6'-methoxy-3,4,5,6-tetrahydro-2H-[1,2']bipyridylyl-3'-ylamine;
   2-(3'-amino-6'-methoxy-3,4,5,6-tetrahydro-2H-[1,2']bipyridylyl-2-yl)ethanol;
   6-methoxy-2-(4-methylpiperazin-1-yl)pyrid-3-ylamine;
   6'-methoxy-2-methyl-3,4,5,6-tetrahydro-2H-[1,2']bipyridylyl-3'-ylamine;
   6'-methoxy-3-methyl-3,4,5,6-tetrahydro-2H-[1,2']bipyridylyl-3'-ylamine;
   2-(3'-amino-6'-methoxy-3,4,5,6-tetrahydro-2H-[1,2']bipyridylyl-2-yl)ethanol, and the addition salts thereof.

7. The composition according to claim 1, wherein the at least one coupler is chosen from 6-methoxy-2-pyrrolidin-1-ylpyrid-3-ylamine and the addition salts thereof.

8. The composition according to claim 1, wherein the at least one oxidation base is chosen from para-phenylenediamines, bis(phenyl)alkylenediamines, para-aminophenols, ortho-aminophenols and heterocyclic bases, and the addition salts thereof.

9. The composition according to claim 1, wherein the at least one oxidation base is present in an amount ranging from 0.001% to 10% by weight, relative to the total weight of the dye composition.

10. The composition according to claim 1, wherein the at least one coupler is present in an amount ranging from 0.001% to 10% by weight, relative to the total weight of the composition.

11. The composition according to claim 1, further comprising at least one additional coupler chosen from meta-phenylenediamines, meta-aminophenols, meta-diphenols, naphthalenic couplers, heterocyclic couplers, and the addition salts thereof.

12. The composition according to claim 11, wherein the at least one additional coupler is present in an amount ranging from 0.001% to 10% by weight, relative to the total weight of the dye composition.

13. The composition according to claim 1, further comprising at least one direct dye chosen from nitrobenzene, cationic, azo, and methine dyes.

14. A process for oxidation dyeing of keratin fibers, comprising applying to the keratin fibers at least one dye composition comprising, in a medium suitable for dyeing, at least one oxidation base, and at least one coupler chosen from 6-alkoxy-2,3-diaminopyridine derivatives of formula (I) and the addition salts thereof:

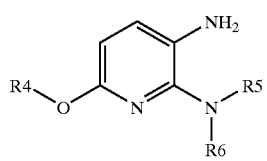

Formula (I)

wherein:

$R_4$ is chosen from $C_1$–$C_4$ alkyl radicals optionally substituted with at least one radical chosen from hydroxyl, $C_1$–$C_2$ alkoxy and $NR_7R_8$ radicals, wherein $R_7$ and $R_8$, which may be identical or different, are each chosen from hydrogen and $C_1$–$C_4$ alkyl, $C_2$–$C_6$ (poly)hydroxyalkyl, $C_2$–$C_6$ (poly)aminoalkyl and $C_2$–$C_6$ aminohydroxyalkyl radicals;

$R_5$ and $R_6$ form, together with the nitrogen atom to which they are attached, a carbon ring chosen from 5- to 8-membered rings, wherein at least one carbon atom of the 5- to 8-membered rings may be replaced with at least one entity chosen from an oxygen atom, an optionally substituted nitrogen atom, a sulphur atom, and an $SO_2$ group; at least one carbon atom of the 5- to 8-membered rings may, independently of each other, be substituted; and said 5- to 8-membered rings do not comprise a peroxide bond, a diazo radical or a nitroso radical;

and at least one oxidizing agent.

15. The process according to claim 14, wherein the at least one oxidizing agent is chosen from hydrogen peroxide, urea peroxide, alkali metal bromates, persalts, peracids and oxidase enzymes.

16. The process according to claim 14, comprising mixing, at the time of use, the at least one oxidizing agent with the at least one dye composition.

17. A process for oxidation dyeing of keratin fibers, comprising applying to the keratin fibers at least one oxidizing composition comprising, in a medium suitable for dyeing, at least one oxidizing agent, simultaneously with or sequentially to at least one dye composition comprising, in a medium suitable for dyeing, at least one oxidation base, and at least one coupler chosen from 6-alkoxy-2,3-diaminopyridine derivatives of formula (I) and the addition salts thereof:

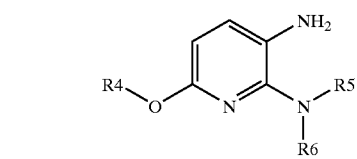

Formula (I)

wherein:

$R_4$ is chosen from $C_1$–$C_4$ alkyl radicals optionally substituted with at least one radical chosen from hydroxyl, $C_1$–$C_2$ alkoxy and $NR_7R_8$ radicals, wherein $R_7$ and $R_8$, which may be identical or different, are each chosen from hydrogen and $C_1$–$C_4$ alkyl, $C_2$–$C_6$ (poly)hydroxyalkyl, $C_2$–$C_6$ (poly)aminoalkyl and $C_2$–$C_6$ aminohydroxyalkyl radicals;

$R_5$ and $R_6$ form, together with the nitrogen atom to which they are attached, a carbon ring chosen from 5- to 8-membered rings, wherein at least one carbon atom of the 5- to 8-membered rings may be replaced with at least one entity chosen from an oxygen atom, an optionally substituted nitrogen atom, a sulphur atom, and an $SO_2$ group; at least one carbon atom of the 5- to 8-membered rings may, independently of each other, be substituted; and said 5- to 8-membered rings do not comprise a peroxide bond, a diazo radical or a nitroso radical.

18. A multi-compartment kit or device comprising a first compartment comprising at least one dye composition comprising, in a medium suitable for dyeing, at least one oxidation base, and at least one coupler chosen from 6-alkoxy-2,3-diaminopyridine derivatives of formula (I) and the addition salts thereof:

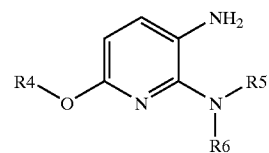

Formula (I)

wherein:

$R_4$ is chosen from $C_1$–$C_4$ alkyl radicals optionally substituted with at least one radical chosen from hydroxyl, $C_1$–$C_2$ alkoxy and $NR_7R_8$ radicals, wherein $R_7$ and $R_8$, which may be identical or different, are each chosen from hydrogen and $C_1$–$C_4$ alkyl, $C_2$–$C_6$ (poly)hydroxyalkyl, $C_2$–$C_6$ (poly)aminoalkyl and $C_2$–$C_6$ aminohydroxyalkyl radicals;

$R_5$ and $R_6$ form, together with the nitrogen atom to which they are attached, a carbon ring chosen from 5- to 8-membered rings, wherein at least one carbon atom of the 5- to 8-membered rings may be replaced with at least one entity chosen from an oxygen atom, an optionally substituted nitrogen atom, a sulphur atom, and an $SO_2$ group; at least one carbon atom of the 5- to 8-membered rings may, independently of each other, be substituted; and said 5- to 8-membered rings do not comprise a peroxide bond, a diazo radical or a nitroso radical; and a second compartment comprising at least one oxidizing composition.

19. A process for dyeing keratin fibers comprising contacting said keratin fibers in a medium suitable for dyeing, with at least one oxidation base, and at least one coupler chosen from 6-alkoxy-2,3-diaminopyridine derivatives of formula (I) and the addition salts thereof:

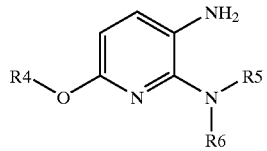

Formula (I)

wherein:

$R_4$ is chosen from $C_1$–$C_4$ alkyl radicals optionally substituted with at least one radical chosen from hydroxyl, $C_1$–$C_2$ alkoxy and $NR_7R_8$ radicals, wherein $R_7$ and $R_8$, which may be identical or different, are each chosen from hydrogen and $C_1$–$C_4$ alkyl, $C_2$–$C_6$ (poly)hydroxyalkyl, $C_2$–$C_6$ (poly) aminoalkyl and $C_2$–$C_6$ aminohydroxyalkyl radicals;

$R_5$ and $R_6$ form, together with the nitrogen atom to which they are attached, a carbon ring chosen from 5- to 8-membered rings, wherein at least one carbon atom of the 5- to 8-membered rings may be replaced with at least one entity chosen from an oxygen atom, an optionally substituted nitrogen atom, a sulphur atom, and an $SO_2$ group; at least one carbon atom of the 5- to 8-membered rings may, independently of each other, be substituted; and said 5- to 8-membered rings do not comprise a peroxide bond, a diazo radical or a nitroso radical.

20. At least one entity chosen from 6-alkoxy-2,3-diaminopyridine derivatives of formula (I) below and the addition salts thereof:

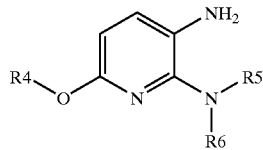

Formula (I)

wherein:

$R_4$ is chosen from $C_1$–$C_4$ alkyl radicals optionally substituted with at least one radical chosen from hydroxyl, $C_1$–$C_2$ alkoxy and $NR_7R_8$ radicals, wherein $R_7$ and $R_8$, which may be identical or different, are each chosen from hydrogen and $C_1$–$C_4$ alkyl, $C_2$–$C_6$ (poly)hydroxyalkyl, $C_2$–$C_6$ (poly)aminoalkyl and $C_2$–$C_6$ aminohydroxyalkyl radicals;

$R_5$ and $R_6$ form, together with the nitrogen atom to which they are attached, a carbon ring chosen from 5- to 8-membered rings, wherein at least one carbon atom of the 5- to 8-membered rings may be replaced with at least one entity chosen from an oxygen atom, an optionally substituted nitrogen atom, a sulphur atom, and an $SO_2$ group; at least one carbon atom of the 5- to 8-membered rings may, independently of each other, be substituted; and said 5- to 8-membered rings do not comprise a peroxide bond, a diazo radical or a nitroso radical; with a proviso that said at least one entity is not chosen from 3-amino 6-methoxy 2-(4-methyl 2-propylimidazol-1-yl)-pyridine, and 3-amino 6-methoxy 2-pyrrolo-pyridine.

21. The at least one entity according to claim 20, wherein $R_5$ and $R_6$ form, together with the nitrogen atom to which they are attached, a heterocycle chosen from 5- to 8-membered heterocycles chosen from pyrrolidine, piperidine, homopiperidine, piperazine, homopiperazine and diazepane heterocycles.

22. The at least one entity according to claim 20, wherein said 5- to 8-membered rings are optionally substituted with at least one radical chosen from the following radicals:
(i) $C_1$–$C_4$ alkyl optionally substituted with at least one radical chosen from hydroxyl, amino, $C_1$–$C_2$ (di)alkylamino and carboxyl radicals;
(ii) hydroxyl;
(iii) amino;
(iv) $C_1$–$C_2$ (di)alkylamino;
(v) carboxyl;
(vi) carboxamido; and
(vii) sulphonamido.

23. The at least one entity according to claim 20, wherein $R_5$ and $R_6$ form, together with the nitrogen to which they are attached, a heterocycle chosen from 2,5-dimethylpyrrolidine, proline, 3-hydroxyproline, 4-hydroxyproline, 2,4-dicarboxypyrrolidine, 3-hydroxy-2-hydroxymethylpyrrolidine, 2-carboxamidopyrrolidine, 3-hydroxy-2-carboxamidopyrrolidine, 2-(diethylcarboxamido)pyrrolidine, 2-hydroxymethylpyrrolidine, 3,4-dihydroxy-2-hydroxymethylpyrrolidine, 3-hydroxypyrrolidine, 3,4-dihydroxypyrrolidine, 3-aminopyrrolidine, 3-methylaminopyrrolidine, 4-amino-3-hydroxypyrrolidine, 3-hydroxy-4-(2-hydroxyethyl)-aminopyrrolidine, 2,6-dimethylpiperidine, 2-carboxypiperidine, 2-carboxamidopiperidine, 2-hydroxymethylpiperidine, 3-hydroxy-2-hydroxymethylpiperidie, 3-hydroxypiperidine, 4-hydroxypiperidine, 3-hydroxy-methylpiperidine, homopiperidine, 2-carboxyhomo-piperidine, 2-carboxamidohomopiperidine, diazepane, N-methyldiazepane, N-(2-hydroxyethyl)diazepane, and the addition salts thereof.

24. The at least one entity according to claim 20, wherein $R_5$ and $R_6$ form, together with the nitrogen to which they are attached, a heterocycle chosen from pyrrolidine, 3-hydroxypyrrolidine, 3-aminopyrrolidine, 3-acetamidopyrrolidine, 3-(methylsulphonylamino) pyrrolidine, proline, 3-hydroxyproline, piperidine, hydroxypiperidines, homopiperidine, diazepane, N-methylhomopiperazine and N-β-hydroxyethylhomopiperazine, and the addition salts thereof.

25. The at least one entity according to claim 20, chosen from:
6-methoxy-2-pyrrolidin-1-ylpyrid-3-ylamine;
2-(2,5-dimethylpyrrolidin-1-yl)-6-methoxypyrid-3-ylamine;
6-methoxy-2-morpholin-4-ylpyrid-3-ylamine;
N-[1-(3-amino-6-methoxypyrid-2-yl)pyrrolidin-3-yl]acetamide;
6'-methoxy-3,4,5,6-tetrahydro-2H-[1,2']bipyridylyl-3'-ylamine;
2-(3'-amino-6'-methoxy-3,4,5,6-tetrahydro-2H-[1,2']bipyridylyl-2-yl)ethanol;
6-methoxy-2-(4-methylpiperazin-1-yl)pyrid-3-ylamine;
6'-methoxy-2-methyl-3,4,5,6-tetrahydro-2H-[1,2']bipyridylyl-3'-ylamine;
6'-methoxy-3-methyl-3,4,5,6-tetrahydro-2H-[1,2']bipyridylyl-3'-ylamine;
2-(3'-amino-6'-methoxy-3,4,5,6-tetrahydro-2H-[1,2']bipyridylyl-2-yl)ethanol, and the addition salts thereof.

26. A process for manufacturing a dye composition comprising including in said dye composition, at least one oxidation base, and at least one coupler chosen from 6-alkoxy-2,3-diaminopyridine derivatives of formula (I) and the addition salts thereof:

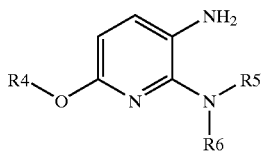

Formula (I)

wherein:

$R_4$ is chosen from $C_1$–$C_4$ alkyl radicals optionally substituted with at least one radical chosen from hydroxyl, $C_1$–$C_2$ alkoxy and $NR_7R_8$ radicals, wherein $R_7$ and $R_8$, which may be identical or different, are each chosen from hydrogen and $C_1$–$C_4$ alkyl, $C_2$–$C_6$ (poly)hydroxyalkyl, $C_2$–$C_6$ (poly)aminoalkyl and $C_2$–$C_6$ aminohydroxyalkyl radicals;

$R_5$ and $R_6$ form, together with the nitrogen atom to which they are attached, a carbon ring chosen from 5- to 8-membered rings, wherein at least one carbon atom of the 5- to 8-membered rings may be replaced with at least one entity chosen from an oxygen atom, an optionally substituted nitrogen atom, a sulphur atom, and an $SO_2$ group; at least one carbon atom of the 5- to 8-membered rings may, independently of each other, be substituted; and said 5- to 8-membered rings do not comprise a peroxide bond, a diazo radical or a nitroso radical.

* * * * *

UNITED STATES PATENT AND TRADEMARK OFFICE
CERTIFICATE OF CORRECTION

PATENT NO. : 6,916,345 B2
DATED : July 12, 2005
INVENTOR(S) : Laurent Vidal et al.

It is certified that error appears in the above-identified patent and that said Letters Patent is hereby corrected as shown below:

Column 18,
Line 35, replace "6-methoxy-2-morphoin-4-ylpyrid-3-ylamine," with
-- 6-methoxy-2-morpholin-4-ylpyrid-3-ylamine; --;

Column 22,
Line 33, replace "hydroxymethylpiperidie," with -- hydroxymethylpiperidine, --.

Signed and Sealed this

Thirteenth Day of September, 2005

JON W. DUDAS
*Director of the United States Patent and Trademark Office*